(12) United States Patent  (10) Patent No.: US 8,648,724 B2
Forsberg et al.  (45) Date of Patent: Feb. 11, 2014

(54) SYSTEM AND METHOD FOR MOTIVATING OR PROMPTING HAND WASHING

(76) Inventors: Lars Forsberg, Lyngby (DK); Peter B. Andersen, Lyngby (DK); Murad Mahmoud, København S (DK); Anders Nuchnua Jørgensen, København N (DK)

( * ) Notice: Subject to any disclaimer, the term of this patent is extended or adjusted under 35 U.S.C. 154(b) by 0 days.

(21) Appl. No.: 13/421,763

(22) Filed: Mar. 15, 2012

(65) Prior Publication Data

US 2012/0212344 A1 Aug. 23, 2012

(30) Foreign Application Priority Data

Sep. 16, 2009 (DK) .................................. 2009 01033

(51) Int. Cl.
| | | |
|---|---|---|
| *E03D 5/10* | (2006.01) | |
| *E03D 1/10* | (2006.01) | |
| *G08B 23/00* | (2006.01) | |
| *G05B 19/00* | (2006.01) | |
| *G08B 3/00* | (2006.01) | |
| *G08B 25/08* | (2006.01) | |
| *G08B 21/00* | (2006.01) | |

(52) U.S. Cl.
USPC ............... 340/573.1; 340/5.61; 340/691.1; 340/692; 340/540; 4/300; 4/406

(58) Field of Classification Search
None
See application file for complete search history.

(56) References Cited

U.S. PATENT DOCUMENTS

| | | | |
|---|---|---|---|
| 5,870,015 A | 2/1999 | Hinkel | 340/573 |
| 6,028,520 A | 2/2000 | Maehre | 340/573.1 |
| 6,392,546 B1 * | 5/2002 | Smith | 340/573.1 |
| 6,417,773 B1 | 7/2002 | Vlahos et al. | 340/573.1 |
| 6,956,498 B1 * | 10/2005 | Gauthier et al. | 340/12.51 |
| 7,478,041 B2 * | 1/2009 | Ichikawa et al. | 704/233 |
| 8,237,558 B2 * | 8/2012 | Seyed Momen et al. | 340/539.11 |
| 8,344,893 B1 * | 1/2013 | Drammeh | 340/573.1 |
| 2002/0135486 A1 | 9/2002 | Brohagen et al. | 340/573.1 |
| 2006/0191068 A1 | 8/2006 | Vlahos et al. | 4/661 |
| 2009/0195385 A1 * | 8/2009 | Huang et al. | 340/573.1 |
| 2009/0273477 A1 * | 11/2009 | Barnhill | 340/573.1 |
| 2009/0299782 A1 * | 12/2009 | Cantor et al. | 705/7 |
| 2010/0045461 A1 * | 2/2010 | Caler et al. | 340/541 |
| 2010/0073162 A1 * | 3/2010 | Johnson et al. | 340/540 |
| 2011/0273298 A1 * | 11/2011 | Snodgrass et al. | 340/573.1 |

FOREIGN PATENT DOCUMENTS

| | | |
|---|---|---|
| GB | 2 425 388 | 10/2006 |
| WO | WO 2002/077927 A1 | 10/2002 |
| WO | WO 2008/034446 A2 | 3/2008 |

OTHER PUBLICATIONS

International Search Report, PCT/DK2010/050238, mailed Mar. 14, 2011.
International Preliminary Report on Patentability, PCT/DK2010/050238.
Judah G., et al., "Experimental Pretesting of Hand-Washing Interventions in a Natural Setting", American Journal of Public Health, vol. 99, No. S2, pp. 405-411 (2009).

* cited by examiner

*Primary Examiner* — George Bugg
*Assistant Examiner* — Renee Dorsey
(74) *Attorney, Agent, or Firm* — Winston & Strawn LLP

(57) ABSTRACT

The invention relates to a system and method for motivating or prompting persons to wash hands. The system includes a sensor for detecting use of a toilet or a urinal, which sensor creates a first signal indicative of that use, and a signaling arrangement for issuing in response to the first signal at least one second signal reminding or prompting the person to use a cleansing agent dispenser.

32 Claims, 7 Drawing Sheets

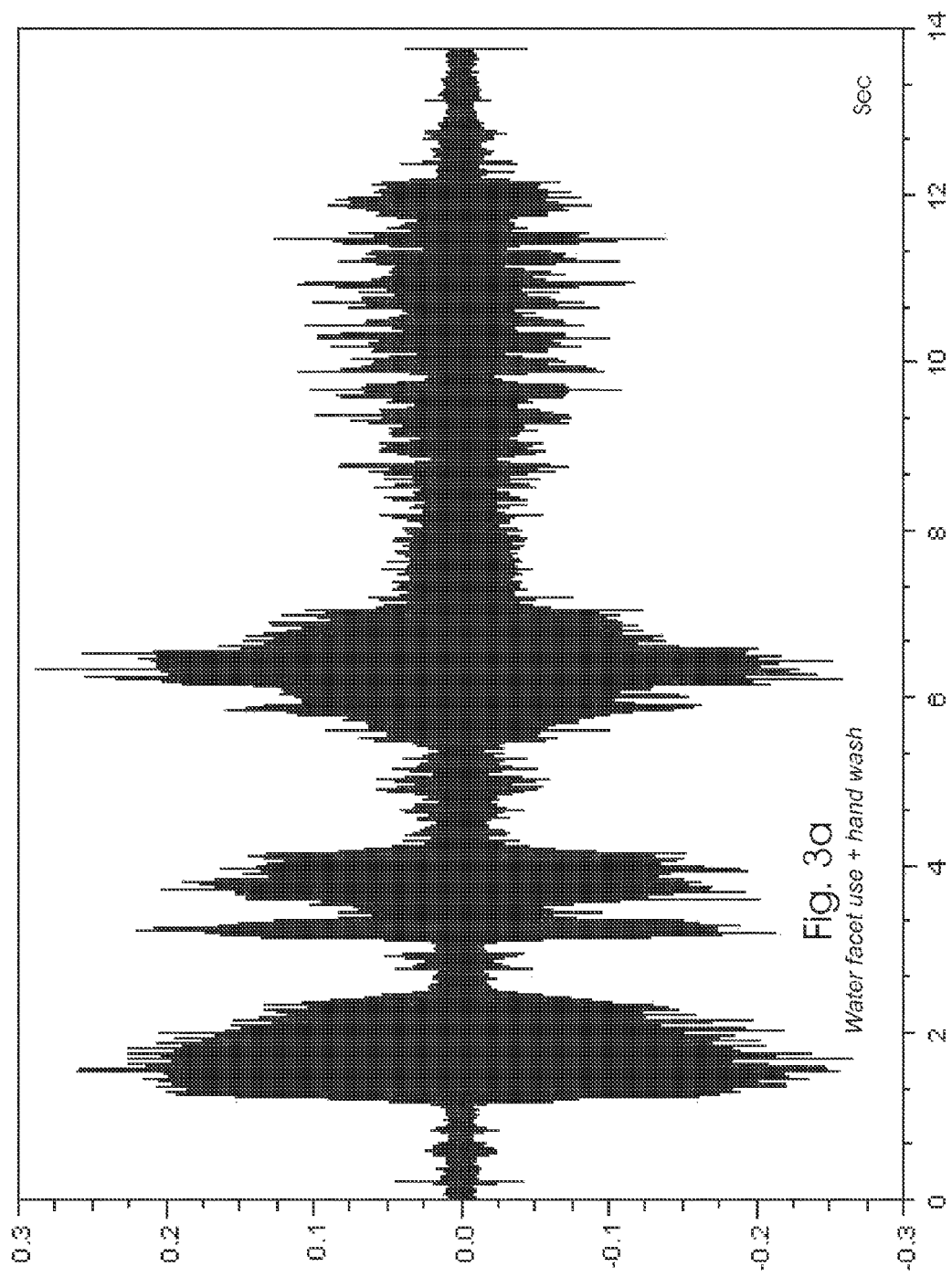

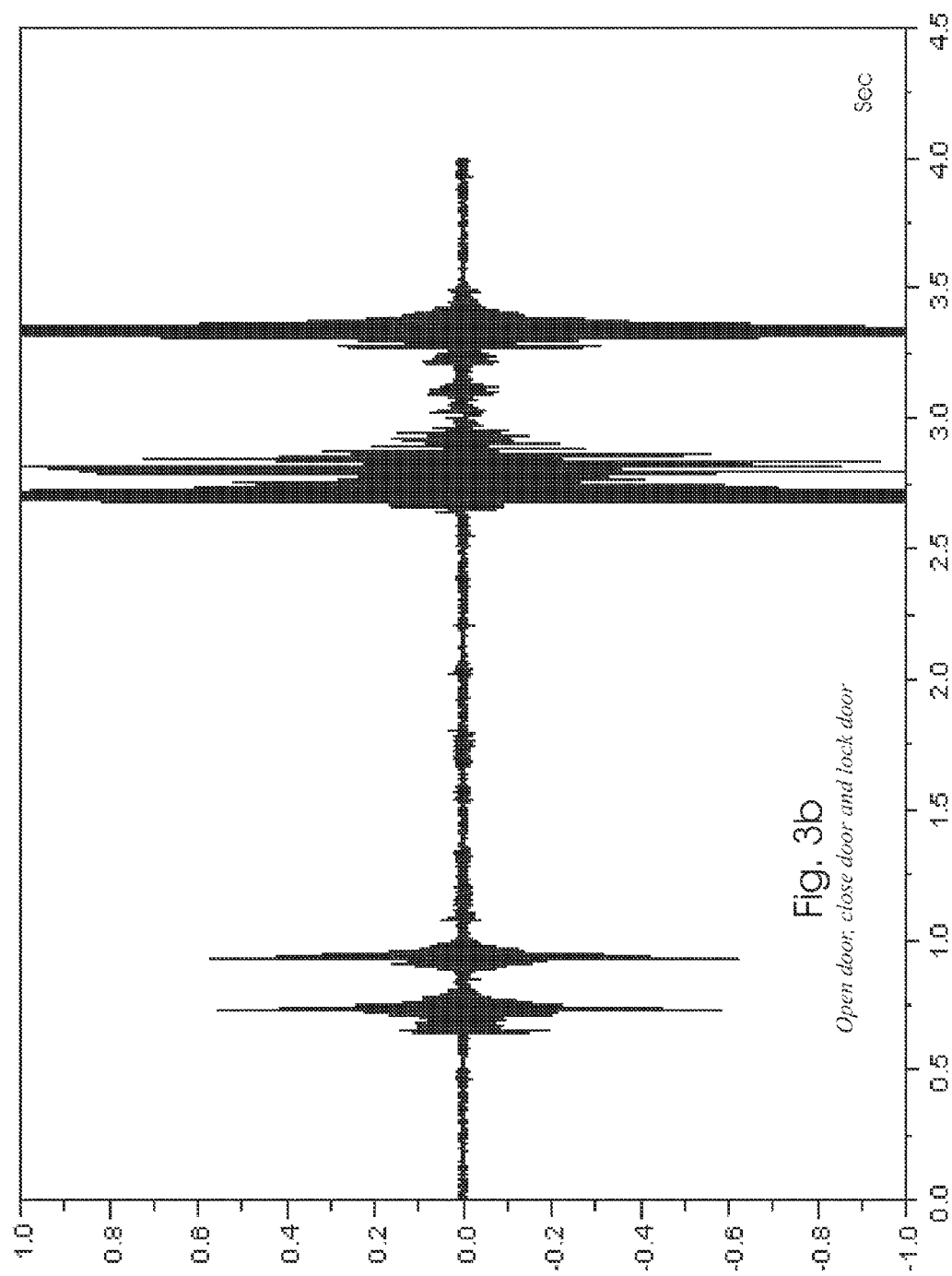

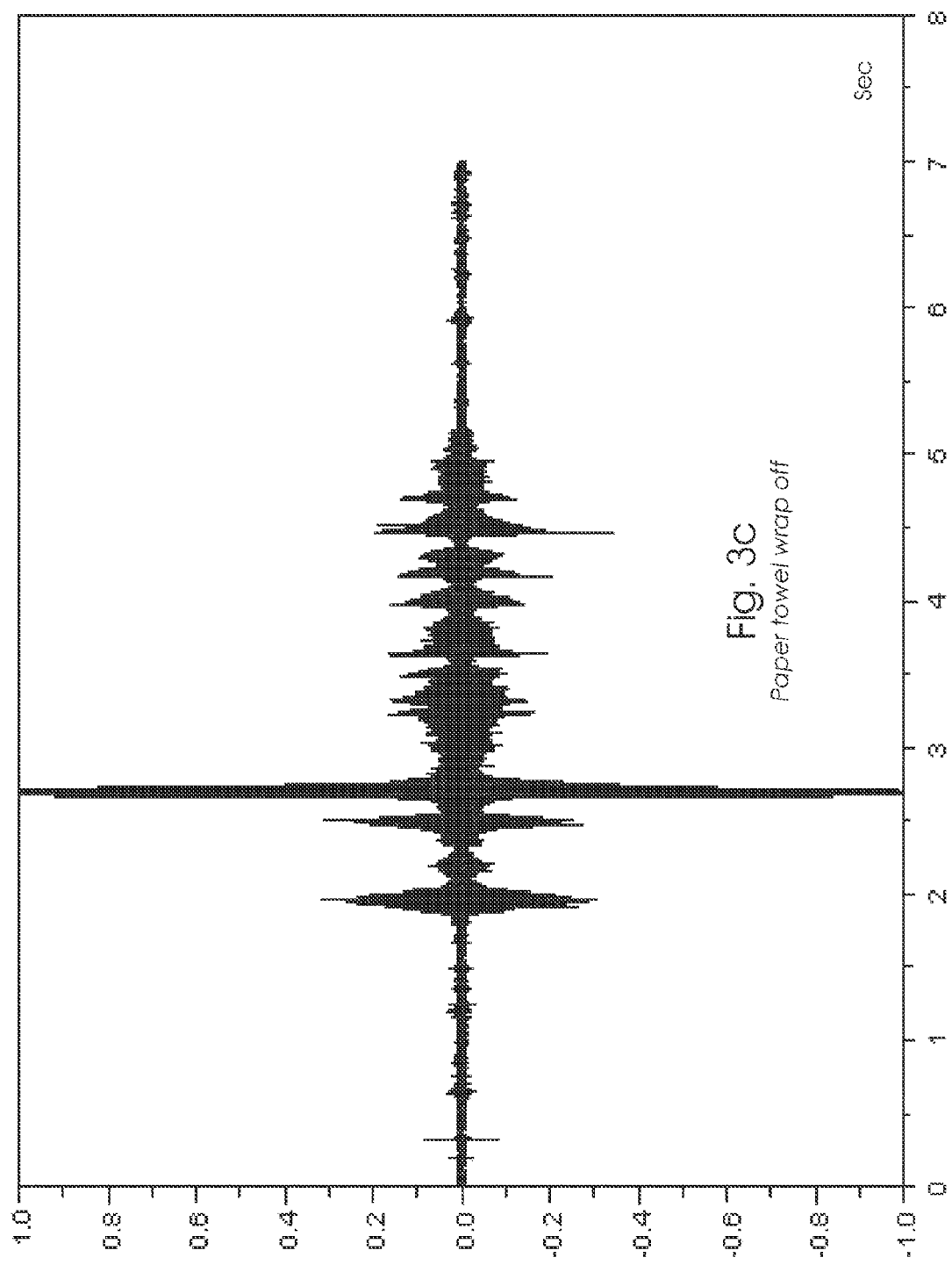

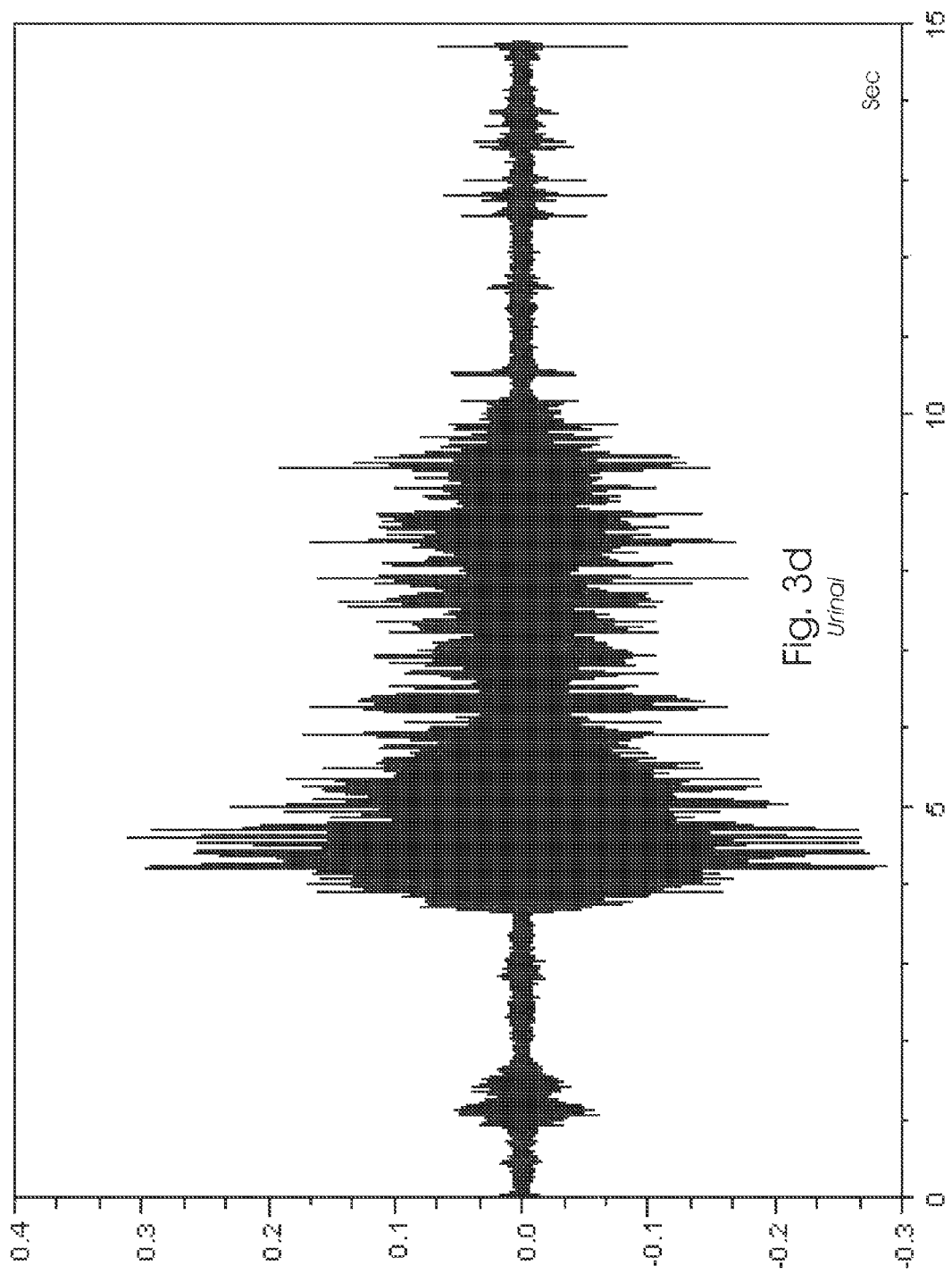

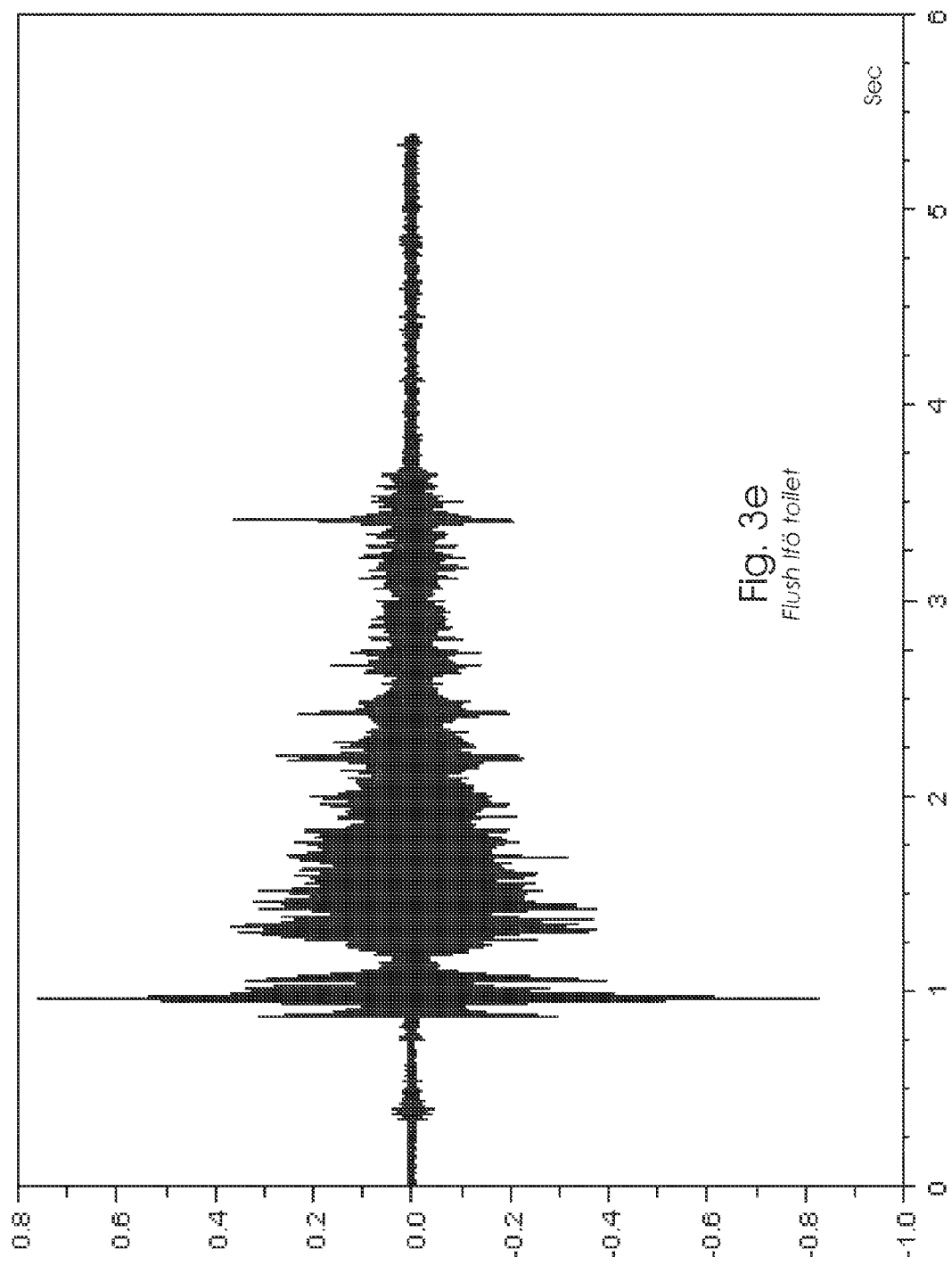

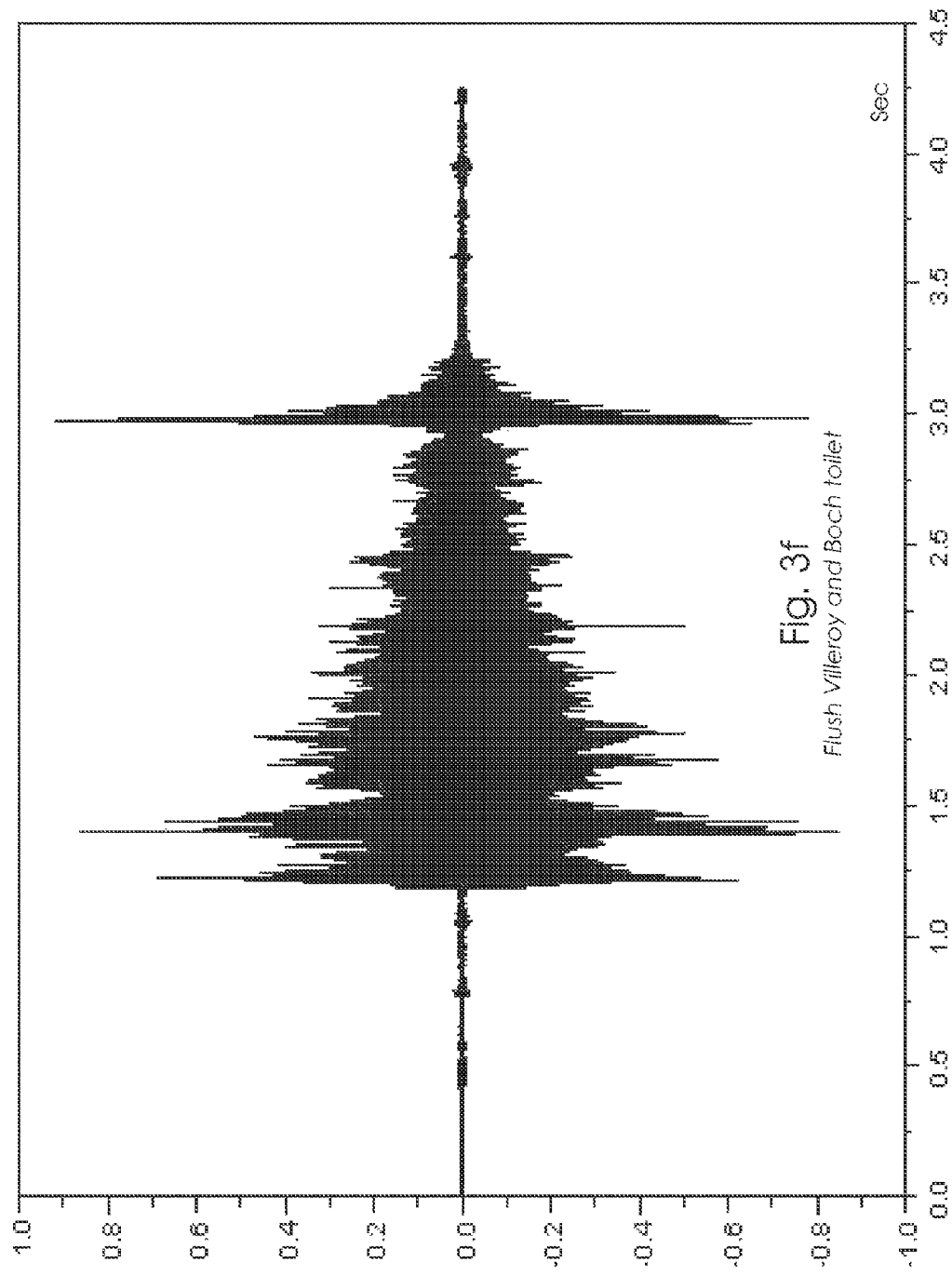

SYSTEM AND METHOD FOR MOTIVATING OR PROMPTING HAND WASHING

CROSS-REFERENCE TO RELATED APPLICATIONS

This application is a continuation of 371 filing of International Patent Application PCT/DK2010/050238 filed Sep. 16, 2010, the entire content of which is expressly incorporated herein by reference thereto.

BACKGROUND

The present invention relates to a system for motivating and/or prompting persons to wash hands, the system comprises a sensor means for detecting use of a toilet or a urinal, which sensor means creates a first signal indicative of that use have been detected, a signaling means for in response to the first signal issuing at least one second signal reminding and/or prompting persons to use a cleansing agent dispenser, and a first transmitter means for transmitting the first signal obtained by the sensor means to the signaling means.

In particular the present invention relates to a system for motivating and/or prompting persons to wash hands subsequent to having used a toilet or a urinal.

Infectious diseases, such as the common cold, flu and gastrointestinal disorders, such as infectious diarrhea are commonly spread through direct or indirect contact to other people. Germs accumulate on the hands from a variety of sources, including direct hand-to-hand contact and touching surfaces other people have touched. Many people do not practice hand washing or only brief hand washing after having used the toilet. Such people are highly responsible for spreading germs and/or contributing to food-related illnesses, such as *Salmonella* and *E. coli* infection. Even though most people intend to wash their hands regularly, including after visiting the toilet, the hand-washing technique is inadequate and still not a routine action for many persons. In particular children's minds are occupied by other thoughts and children often forget to wash hands. Furthermore, only rarely adults and children demonstrate a sufficient level of scrupulous hand washing to prevent spreading germs. The hands are not rubbed long enough and not all areas of the hands are scrubbed. In summary hand hygiene, in particular after having used the toilet, is lacking or inadequate, and potentially lethal bacterial and viral epidemics becomes more and more frequent due to bad hand hygiene.

Studies reported in "Experimental Pretesting of Hand-Washing Interventions in a Natural Setting" by Gaby Judah et al., American Journal of Public Health, October 2009, Vol 99, No. S2 p. 405-411, concludes that observation of behavior in a natural setting can help identify the most effective interventions for changing behaviors of public health importance. It was realized that public health interventions should target to men and women differently. Studies have revealed that 25% men and 16% women do not wash hands subsequent to having used the toilet. Further, only 30-35% of these men and women use soap or other cleansing agent for handwashing.

The recent global outbreak of a new strain of influenza A virus subtype H1N1 has made great immediate interest in better systems for inciting and encouraging handwashing.

Known simple measures to encourage hand washing is to put up signs or posters with encouraging information, advices and hints, but most people overlook such information that just becomes part of environment. Another serious problem is that people who actually wash their hands, despite the good intentions do not use a sufficient period of time to ensure germicidal effect to prevent contamination and infection of surroundings.

British patent application no. GB 2425388 A discloses a system for motivating people to wash their hands. A washroom has means to detect the presence of a user by way of entry and exit. The washroom also includes sensors to monitor the use of hand washing. A soap dispenser includes a sensor and a transmitter to signal the event of the dispenser having been used, indicating that hands have been washed in a basin. An alarm is operated if the user exits without having used the dispenser. This known system counts and registers the number of persons entering and exiting the washroom, and compares this number with the number of activations of the soap dispenser. In case of discrepancy an alert is triggered and signals transmitted into the environment. Users are equipped with each their tag to keep records of users individual behavior.

This known system is concerned with registration of the numbers of events and not how effective the event is accomplished. The entrance of a person into the washroom, and not the action of using the toilet, is linked to the soap dispenser and a signal is transmitted once the soap dispenser has been used. Thus this system has no encouragement to wash hand. Further this known system has no measures for motivating towards an appropriate long washing period.

US patent publication US2006191068 discloses a system for encouraging the practice of good hygiene. After use of a tankless toilet, where water is directly admitted from a water supply line into the toilet bowl the user is reminded by a recorded message to thoroughly cleanse his or her hands before leaving. The recorded message is triggered by a surface temperature change of the conduit between the flush valve of the tankless toilet and the toilet bowl. The temperature sensor provides an output signal indicative of the surface temperature of the conduit. The sensor is interrogated at successive predetermined intervals. Means are provided for comparing the output signal of the sensor at the beginning of one interval with the same signal at the beginning of a succeeding interval, and if a change in temperature occurs, another signal is generated which triggers a pre-recorded message, generated by a voice chip and a speaker, urging the toilet user to wash his or her hands. This known system relies on a surface temperature change in the conduit between the flush valve of the tankless toilet and the toilet bowl when water flushes through the normally empty conduit. Since the standing flushwater, that initially enters the toilet bowl when flushing, is heated by the surroundings, the standing flushwater in the conduit and the conduit itself often may reach the same temperature, in particular if the toilet has not been used for some time. Under such circumstances no temperature change can be registered and this system does not perform according to the intention. Moreover, the system requires either prior installation of the temperature sensor or demounting of the conduit for later installation of the sensor. Thus implementation and use of this known system may involve considerable installation costs as well as the system may be unreliable under some temperature and use conditions.

U.S. Pat. No. 6,028,520 relates to an annunciator for a toilet having a seat and a flush handle. The annunciator plays one or more specific prerecorded messages from a number of stored messages. The specific message or messages played are determined by the sensed toilet conditions including operation of the flush handle; occupation of the toilet seat; position of the toilet seat; and proximity of a person to the toilet. These sensed conditions can be measured using a.o. motion detectors and pressure switches to be logically combined to play messages that are particularly suited to the events taking place with respect to the toilet. The annunciator is housed in a plastic housing hanging on the side of a toilet tank under the tank lid, is incorporated into the seat of the toilet or hangs from the flush handle of the toilet. Externally accessible components on the housing include a speaker, a volume control, an on/off switch, and an infrared motion detector. An electrical cable having a pair of electrical wires leads to a flush sensor that provides an indication that the flush handle has been depressed. A second pair of wires leads to a pressure sensor in the toilet seat that detects a person sitting on the seat, while a third pair of wires leads to a tilt sensor that detects whether the seat is raised or lowered on the bowl. This known device is inserted in close proximity to the toilet and exterior to the toilet, so that the device is easy to access for example to exchange the battery. There is however a great risk that the wires are accidentally teared off the device by a person, such as the toilet user or the cleaner, who accidentally disconnects the respective sensors. Thus, although this known annunciator can be mounted on existing installations it has the disadvantage of the complex wired structure. Furthermore, due to the direct mounting on the toilet or on parts of the toilet the annunciator constitutes a surface for deposition on contaminating and infectious matter from toilet users and is in itself unhygienic.

Also U.S. Pat. No. 5,870,015 discloses an apparatus for instructing a person in the use of a toilet and associated personal hygiene. The apparatus includes a housing, which is attachable to a tank cover of a toilet reservoir tank or to other part of the toilet, e.g. using a suction cup. A switch arm extending from the housing is adapted to mechanically couple with the toilet flushing mechanism. An audio speaker is partly enclosed within the housing and produces the audible message. Electronic circuitry enclosed within the housing receives a switch activity signal indicative of the position of the switch arm and responsively activates production of the audible message. A detector unit is adapted to monitor toilet use activity and to produce a detect signal upon detecting such activity. A control unit receives the detect signal and produces a control signal in response thereto. A message storage unit receives the control signal and responsively produces a message signal. A message output unit receives the message signal and produces a corresponding audible message. The message storage unit produces a plurality of message signals, each corresponding with a respective one of a plurality of recorded messages stored in the message storage unit. Selected ones of these messages are then provided to the person in response to detecting toilet use activity. A separate audio speaker may be associated with a sink to provide time-delayed instructions regarding handwashing, relative to the first message, or can itself be activated in response to a signal produced by a separate sensor detecting, for example, a person's motion away from the toilet or near the sink. However motions sensors registering motion in the vicinity of the toilet or near the sink may trigger a lot of false signals not related to actual use of the toilet causing embarrassment to such unlucky people, e.g. people that just accompanies a toilet user, or just want to use a mirror, etc. The mounting on the tank cover is also not hygienic. Moreover, this simple mechanical principle will not function in case the toilet cannot flush.

U.S. Pat. No. 6,417,773 discloses a system for encouraging good personal hygiene by users of toilet facilities. The system comprises a microphone that is positioned to intercept the sound generated by the flushing toilet, an amplifier, a controller, a voice chip or other audio storage means, and a speaker. The audio signal detected by the microphone is converted to an electrical signal, which is fed to an amplifier. It is common knowledge that a transmitted analog audio signal fades gradually during its transmission path and that an amplifier is needed to reconstruct the analog signal. However amplifiers often add non-linearities that distort the actual signal, for which reason the amplified electrical signal also needs to be filtered and modified by a pulse shaper, in an attempt to isolate a characteristic time-frequency signature of a flushing toilet from extraneous noise. Due to relying solely on analog technique this known system is unreliable, a.o. due to amplification errors and low ability to differentiate between signal and noise. Moreover the microphone and the other components are combined in a unit contained in a compact case for mounting on the ceiling of the toilet facility or at another location out of convenient reach by toilet users, to discourage tampering and vandalism, and a message is issued from this toilet user-inaccessible location. This known system does suffer from the major disadvantage that there is no awards, consequence or penalties to the toilet user if the toilet user does not wash his/hers hands in response to the message. As with all prior art systems, this known system also lacks means and/or guidance to ensure that the toilet user in fact washes his/hers hands instead of just leaves the toilet facility subsequent to using it. The teaching of U.S. Pat. No. 6,417,773 discourages to mount components of the system within reach of the toilet user.

Many other measures have been implemented during the years to control hand washing and incite persons to more frequent and effective hand washing, but all known systems suffer from at least one or more of the above disadvantages. The present invention now provides an improved system that overcomes these disadvantages.

SUMMARY OF THE INVENTION

The present invention now provides a system and a method for motivating or prompting persons to wash hands. This system and a method can be used by both adults and children without preceding instructions. In addition, this system and method can be retrofit in existing washrooms and toilet facilities.

In particular, this system and method links actual use of a toilet to a handwashing motivating and or prompting mechanism or procedure. It does not require modification of a toilet or a urinal or the installation of components to be mounted directly on the toilet or urinal or on parts of the toilet or the urinal, including on flush water supply conduits. It also does not require identification of the toilet user for activation or initiation of a handwashing motivating and/or prompting mechanism or procedure. Instead, the system and method of the invention has means to aid in ensuring that the persons in fact washes their hands instead of just leaving the toilet facility subsequent to having used the toilet or urinal. In addition, the invention rewards and/or gives persons that wash their hands after having used a toilet or urinal a good and positive experience such that hand hygiene is improved.

The system and method of the invention thus has a higher operational dependability and reliability than known systems and methods. It is also useful for motivating and/or prompting persons that are visually or audible impaired to wash hands by providing directional guidance towards a cleansing agent dispenser. In addition, the system and method are language independent and is not triggered by false events not related to use of a toilet or urinal.

The novel and unique features of the present invention include sensor means for detecting use of a toilet or urinal, which sensor means creates a first signal indicative of that use have been detected, signaling means for issuing at least one second signal in response to the first signal for reminding or prompting persons to use a cleansing agent dispenser, and first transmitter means for transmitting the first signal obtained by the sensor means to the signaling means. The signaling means is associated with the cleansing agent dispenser, and the system comprises a second transmitter means for, in response to actuation of the cleansing agent dispenser, transmitting a second signal to the signaling means that a dose of cleansing agent has been dispensed In the context of the present invention the term "wash hands" or "hand washing" is used for all acts involving cleansing of hands, including handwashing involving water and soap, but also disinfection actions involving alcohols or alcogels, and combinations of the before mentioned.

Entry into a washroom or toilet room is not synonymous with use of the toilet or urinal. A person may enter a washroom for other purposes such as putting make-up on or changing clothes, etc. Thus an entry sensor means is not suitable for linking use of the toilet or urinal to use of the cleansing agent dispenser, such as a soap dispenser, subsequent to having used the toilet or urinal. By using a sensor means for detecting the actual use of the toilet or urinal, e.g. the flushing of the toilet or the act of urinating into the urinal, and using this detection to activate a signaling means to emit a second signal in the form of a reminder and/or prompting signal to use the cleansing agent dispenser, the use of the toilet or urinal becomes directly linked to the cleansing agent dispenser, which the person has been encouraged to used by the system according to the present invention.

The second signal may be short, long and/or be of any kind that gives the person the encouraging reward of having done what is expected of him/her, namely cleaned or washed hers/his hands.

In a preferred embodiment the system may comprise a switching means to switch off the second signal upon actuation of the cleansing agent dispenser to dispense the cleansing agent. The second signal, i.e. the signal to remind using the cleansing agent dispenser, encourages and prompts the person that have used the toilet or urinal to move towards the cleansing agent dispenser a.o. to see what the message is in case of a visual signal, or in case of a sound signal to deactivate the alerting, embarrassing or irritating reminder signal, prior to leaving the washroom.

The cleansing agent dispenser may e.g. be of the kind having an optical sensor means serving as the switching means, e.g. a photoelectric detector, which needs to be actuated in response to the presence of the person's hands a predetermined distance below the discharge nozzle of the cleansing agent dispenser. Said distance is so short and requires the presence of the person in close proximity to the cleansing agent dispenser, in order for the person being able to actuate said cleansing agent dispenser. The person cannot cheat the system and switch off the second signal without getting cleansing agent on his hand. Thus if the cleansing agent is soap, the person must wash his/hers hands to remove the cleansing agent before leaving the washroom.

Thus the reminder signal may be a sound signal, which the toilet user would like to deactivate without hesitation. The sound signal can e.g. be an oscillation, one or more tunes emitted at one or more sound levels, or a spoken message on one or more languages, or combinations of these. The sound signal needs not be an unpleasant sound, but can be if desired. The reminder signal can also be a message on a display, e.g. a reminding notification or a hand wash or disinfection instruction video, it can be a picture signal, e.g. a series of pictures, which are known and understood by even small children, or it can just be a shift of color, instantaneous, momentarily or gradually. Combinations of various kinds of reminder signals are envisaged within the scope of the present invention to also enable people being visually handicapped or hearing-handicapped of being reminded too.

An audible reminder signal attract the toilet or urinal users towards the source of the sound to deactivate the noise, but a visual reminder signal may have exactly the same effect in that visual reminder signal may encourage the toilet or urinal users to deactivate or change the visual appearance of the signal or just switch it off.

Thus, irrespective of the reminder signal being audible, visible or both, most toilet or urinal users feel obligated to deactivate the reminder signal so that other people do not discover their embarrassing lack of hand wash. The reminder signal may also serve to guide the toilet or urinal users towards the source of the reminder signal, with the further inherent advantageously effect, that the chance that information provided in relation to said source is picked up by the toilet or urinal users is highly improved too.

A preferred second signal comprises both a visual and an audible signal, which preferably may be synchronized, which in the present context means that if the second signal comprises a sound signal that changes, this is reflected in the associated visual signal. For example, if the loudness level of a sound signal increases gradually an associated visual signal, such as the flashing intensity of a light-emitting diode, are correspondingly increased gradually, partly to improve prompting, but also to make very clear wherefrom the second signal is emitted so that everybody, despite or irrespective of intellectual level and ability to perceive and pick up visual and/or audible signals and information in general, is provided with the best possible guidance both directional and instructional.

In one embodiment of the present invention the sensor means can be a sound sensor means for detecting and recognizing at least a part of a sound spectrum associated with the use of the toilet or urinal, which sound sensor means creates a first signal indicative of said sound spectrum has been detected. At least a part of the sound spectrum that is sufficient to associate it with the use of the toilet needs to be detected. Positive detection of the actual event of the toilet or urinal having been used triggers the signaling means to issue the second signal, i.e. the signal reminding to use the cleansing agent dispenser.

In an advantageously embodiment according to the present invention, which is specifically easy to implement in existing toilet facilities and sanitary installation, the sound sensor means can be selected to have auditory discrimination ability.

Such a sound sensor means having auditory discrimination ability can be mounted at any suitable location inside the washroom as long as the sound sensor means is able to detect and recognize the sound of flushing the toilet.

A sound sensing system and method using audio information retrieval from an audio signal is known from International patent application no. WO2008/034446. Sound waves may be either transverse or longitudinal, and solid materials will transmit both kinds, contrary to liquids and gases that only transmit longitudinal waves in the form of a sound wave. Despite the technology described in WO2008/034446 is designed and intended for use with striking solid objects, the inventors of the present invention has surprisingly discovered that the basic principle of the technology described in WO2008/034446 is usable in the present invention too.

Audio information retrieval refers to the retrieval of information from an audio signal. This information can be the underlying content of the audio signal, or information inherent in the audio signal. There is a broad range of categories or classifications that may be used in audio information retrieval, including speech, music, environment sound, and silence. The inventors of the present application have found out that if an input signal can be classified as use of the toilet or the urinal, the obtained result may be used for determining and distinguishing between the various flushing and water related and associated sounds. In the present invention the system and method according to WO2008/034446 may be targeted to a.o. segregate the surrounding noises from at least the flushing sound of the toilet or other sound spectra as described and explained above. The audio signal to be retrieved may also, alternatively or additionally, be a cry for help, in which case the system may be adapted to recognize e.g. the word "help" in various languages and to emit an alert outside the washroom in response to positive identification of the word. The system may be configured in accordance with the language of the environment wherein the system is used. Other kinds of customizations of the system are within the scope of the present invention.

The disclosure of WO2008/034446 does not deal with the complex situation involving sound spectra originating from liquid, interaction between liquid and liquid, or between liquid and solid matter, such as for example when urine or faces hits the water surface in the toilet bowl, or different sound spectra originating from flushing various designs of toilets and urinals, and different sound spectra due to various flushing techniques, such as for example flushing, evacuation, suction and combinations of both, because such sound spectra are very complex. The audio retrieval period for the first signal, which the sensor means need to detect, needs to be longer than known from WO2008/034446 to obtain the necessary characteristics of the complex sound spectra to identify them as uniquely linked to the liquid involving event taking place at the respective toilet or the respective urinal. The training sessions and mathematics described in WO2008/034446 may be extended and/or implemented for the purpose of the present invention to obtain sound spectra data representative of many different toilets, urinals and actions related to their use under various conditions.

In a preferred embodiment the sound sensor means may be selected to have auditory discrimination ability to determine sound spectra relating to at least flushing of water, preferably water flushing a toilet bowl, or water in the bowl or a urinal bowl.

In an alternative embodiment the sound sensor means may be selected to have auditory discrimination ability to determine at least sound spectra relating to water being hit by either a liquid or a solid, or flushing of the toilet or the urinal. The liquid may e.g. be urine and the solid be faeces. Thus the sound spectrum associated with the use of a toilet or a urinal may relate to various actions taken in relation to said use, all of which uses involve contact with and/or flushing of a liquid, normally water and/or urine.

The sensor means may include more than one sensor in order to increase and ensure efficiency. This is e.g. relevant should one of the sensors fail. To that aspect, in an alternative system according to the present invention the sensor means may comprise a water level sensor. In case of use with a flushing toilet a water level sensor may be mounted in the toilet bowl to detect the water level in said bowl. Use of several sensors in the sensor means reduces malfunction to ensure that first signals obtained by the respective sensors of the sensor means are transmitted to the signaling means. The water level sensor can under some circumstances also be the sole sensor means.

The system according to the present invention may comprise means for emission of a wash time period signal upon actuation of the cleansing agent dispenser to dispense the cleansing agent. The wash time period signal may have another sound than the reminder signal, a longer tune, which the person would like to hear to the end, a short story, a joke or the news, or any other information of relevance or interest to the person. In response to activating the cleansing agent dispenser to discharge a dose of cleansing agent the signaling means may e.g. emit the wash time reminder signal in a period selected to correspond to a period of time proven sufficient to wash off infectious matter from the hands. The means for emission of a wash time period signal may be the signaling means that switches to a second mode in which a wash time period signal is emitted.

Both of or any of the reminder signal and/or the wash time period signal may be transmitted as a visual signal on a display, e.g. a short cartoon or movie, a commercial, a piece of information, a change in color etc. The duration of said signal may be selected and targeted to specific uses. In some embodiments there may be none or only a short wash time period signal.

Thus, in an advantageous embodiment that is directed to most users any of the reminder signal and/or the wash time period signal may be signals detectable by auditory sense or faculty of seeing or combination of these senses. In case of the combination both visually and audible impaired persons can be motivated and/or prompted by means of the same system as mentioned above. A sound signal may aid persons having impaired hearing in finding their way to the cleansing agent dispenser and thereby to the washbasin. Auditory and visual information may be combined. For example the visual part could be a color display changing color from light to dark, from red to green etc, and the auditory signal could be a gently increasing tune which becomes easier and easier to hear or fades out the longer the person keeps on washing her/his hands.

The system may advantageously comprise a display for displaying visual information and/or a loud speaker for providing audible information.

The cleansing agent dispenser may be made as a preprogrammed unit or be individually programmable and include conventional and/or common functionalities such as e.g. a level indicator for soap and/or other cleansing agent. Other functions that may be included in the cleansing agent dispenser are a sound alert or other kind of sign or signal if a person stays inside the washroom more than a predetermined period of e.g. 20 minutes. This feature may become relevant in case people gets sick or has an accident. Another feature optionally incorporated in the system according to the present invention is a smoke detector, which becomes relevant in case of fire or people smoking at the washroom. The cleansing agent dispenser may also include means to alert about the need of refilling, counting the number of actuation, counting the number of emitted first signal for a given period, the number of emitted second signal for the same period, and means to compare and relate to any of the detections. In a simple embodiment the first transmitter means also constitutes the second transmitter means.

The preferred use of the system according to the present invention is for a single washroom with one toilet or urinal. If the system according to the present invention is implemented in washrooms having several toilets and/or urinals and thus many visitors, such as e.g. at hospitals, residential homes, swimming baths, fitness centers, schools, restaurants, public institutions, public toilets and many more public places the incidents and risk of indirect transfer of infectious matter from one person to a surface and further from the surface to a lot of other persons or other surfaces can be reduced significantly.

The cleansing agent dispenser may be powered by electricity via its own separate power source or via the public power supply network. The cleansing agent can also be dispensed just by gravity and manual activation of the dispensing function, in which case the gravitational potential energy stored within the system may be utilized to charge e.g. a battery for powering at least some of the many functions of the cleansing agent dispenser.

The system can be powered by either direct current or alternating current. Thus any of battery voltage or line voltage can be used to power the system, including battery voltage of 3V and line voltages of both 110V and 220V-230V, all off which are intended within the scope of the present invention.

The sensor means may include various kinds of sensors. The sensor means may for example comprise one or more sensors selected from a sound sensor having auditory discrimination ability, a level sensor for registering a change in the water level in the toilet flushing cistern or bowl, a flow sensor or a pressure sensor for detecting a change in water pressure and combinations of these. In particular a level sensor, a flow sensor or a pressure sensor may be powered solely or partly by the potential and kinetic energy evolving from the motion of flushing water when the water flushing in the water pipes, the toilet flushing cistern or the toilet basin get in direct contact with or passes by the sensor, or alternatively the sensor means may be incorporated in or be part of the flushing actuator, e.g. a flush button to be depressed, or an optical sensor to be activated for flushing, so that the sensor means in form of the flush activator triggers transmission of the first signal in response to activation of the flush activator.

The system may comprise that the signaling means is associated with the cleansing agent dispenser, preferably provided in the cleansing agent dispenser and/or on the cleansing agent dispenser.

Preferably the display showing a second visual reminder signal or other signal can be provided on the cleansing agent dispenser. Also, a speaker or a microphone emitting a second audible signal reminding to wash hands can be provided in or on the cleansing agent dispenser.

In order that the signaling means stops emitting the second signal, i.e. the reminder signal, e.g. in the situation where the cleansing agent dispenser never is activated and a person has left the washroom ignoring the motivating and/or prompting action of the system, the signaling means may comprise a timer for terminating the reminder signal after a fixed period.

The timer can also be adapted to issue the second signal with a selected delay in response to the first signal having been detected by the sensor means, so that a person having used the toilet or urinal is given a suitable period to compose himself/herself, arrange his/hers clothes, etc. before the second reminder signal is emitted by the signaling means and he/she needs to approach the cleansing agent dispenser to activate it.

The system may comprise a control unit for controlling and/or setting parameters of the system, said control unit may be programmable and either be incorporated in the cleansing agent dispenser or placed remote from the cleansing agent dispenser.

The control unit may be implemented with suitable software for customized controlling of just one single system according to the present invention. The control unit may in the alternative be a separate unit located remote from the cleansing agent dispenser, optionally configured for controlling a plurality of cleansing agent dispensers. The software may include a facility enabling each system and cleansing agent dispenser to be individually configured. For example the reminder signal and/or the wash time period may be longer at one cleansing agent dispenser than at another cleansing agent dispenser and the reminder signal and/or the wash time period signal could be chosen according to knowledge of the group of toilet users to increase susceptibility to activate the cleansing agent dispenser.

Any of the sensor means, the switching means, the first transmitter means, and/or the second transmitter means can also be provided in or on the cleansing agent dispenser. If these means are provided in or on the cleansing agent dispenser, said cleansing agent dispenser appears as, a single, compact multi-unit that is easy to install and replace.

The cleansing agent dispenser may include a cabinet for accommodating the components of the system according to the present invention. The cabinet can be of any size and shape provided it is dimensioned to accommodate the required desired number of components for the system, including the cleansing agent container and the dispenser mechanism.

In an advantageous embodiment including a sound sensor the sound sensor means may comprise at least one microphone for receiving the sound spectrum associated with a sound representative of that the toilet or the urinal has been used. It may preferred that the sound sensor means comprises at least two microphones arranged to receive sound spectra from different directions and sources, in order to be able to segregate noise interfering the relevant sound spectrum, which noise originates from an irrelevant source, to ensure a higher dependability of the system.

In one embodiment the system may comprises a database or register of sound spectra representative of sound spectra associated with the use of the toilet or the urinal. Preferably the sound spectra in the database includes a selection of standard sounds associated with conventional and commercially available toilets and urinals, so that the system can be installed in existing toilet facilities with such commercially known toilets and urinals. The database may however also include sound spectra from customized toilet facilities, as well as other sound spectra that needs to be segregated from the first signal to trigger the second signal without error, so that only the first signal that is indicative of actual use of the toilet and/or urinal triggers the second signal at the right time subsequent to the toilet or urinal having been used and not e.g. is triggered if a door opens and closes or a paper towel is wrapped off.

In case the toilet or urinal is not a conventional one, or the actions, that are performed at the toilet facility and/or the washroom and must be detected by the sensor means, are of a specific kind not normally associated with use of the toilet facility and/or the wash room, and therefore not represented by a sound spectrum in the database, the system may comprise a recording means for recording a sound spectrum associated with one or more specific uses of a specific toilet and/or a specific urinal or other action taken at the toilet facility and/or the washroom, in particular other actions involving a sound relating to liquid. The recording means may thus record the sound spectra representative for one or more specific uses of the specific toilets and/or urinals.

Since sound spectra indicative of use of a toilet, a urinal or other features or actions relating to use of a washroom or toilet facility are much more complex than in the simple case of e.g. the sound spectra originating from contact between two solid materials, the sound spectrum is preferably recorded for a period sufficiently to establish true identification of the use, which period is at least 0.5 second, preferably at least 0.7 second and more preferred at least 1.0 second. This duration of period ensures true identification of use of the toilet or urinal or the above suggested other actions that might be of interest to couple to use of the cleansing agent dispenser, and thus to issuance of the second signal. The selected recording period needs to be sufficiently long to provide a sound spectrum truly indicative of the specific use, and the training sessions as suggested in WO2008/034446 may be beneficial in order to obtain the sound signature of the customized, not previously known, configuration and design of a sanitary installation.

The sound sensor means or the control unit may be configured to compare and differentiate between the sound spectra detected in different directions by the sensor means to avoid false second signals. Accordingly, the sensor means or the control unit may be configured to select the one of the two sound spectra coming from different directions that represents the sound spectrum representative of use of the toilet or the urinal.

The system according to the present invention may comprise storage means for storage of recorded sound spectra and/or other data for operating the system. Examples of storage means includes computer data storage means including but not limited to recording media, RAM, computer disk storage means, including exchangeable disks, such as optical disks, and hard disk drives.

The storage means may be part of a computer means for operating and driving the system. The computer unit may be a microchip, a microprocessor or other conventional commercially available technology with software adapted for at least storing, processing, transmitting and calculating data representing detected first signals and emitted second signals. Preferably the computer means are accommodated or integrated in the cleansing agent dispenser, just at the other means mentioned above.

The cleansing agent may in most washrooms be a soap, preferably a liquid soap, however the cleansing agent can also be an alcohol, an alcohol containing gel, or combinations of the before mentioned. In case of combinations use of an alcohol containing cleansing agent may be a supplemental offer to the user of the toilet or urinal, in which case a separate alcohol containing cleansing agent dispenser may be arranged next to the cleansing agent dispenser that needs to be activated in order to stop or change the second signal to remind to wash hands. The alcohol containing cleansing agent dispenser may however also be the dispenser allocated to issuance of the second signal.

Soap may e.g. contain a plain liquid soap or a germicidal liquid soap. It is however often not realized or intentionally neglected that various spots, such as between fingers, need more attention during washing. To this aspect the cleansing agent dispenser may contain a fluorescent soap and the system comprise a means for detecting fluorescence radiation in order for the person washing his/hers hands to subsequently confirm the degree of cleanness of the washed hands. In case the hands are still fluorescent the person is triggered to wash his/hers hands once more.

The system according to the present invention is not dependent on motion sensors for detection of motion of a person in the vicinity of the toilet or the urinal in order to detect use of the toilet or urinal. The personal identity and/or behavior of the individual toilet or urinal users are not disclosed nor reported nor registered in one embodiment of the system according to the present invention. The identity of the toilet or urinal users remains always anonym to the inventive system, which provides a unique opportunity for researchers to make statistics of human handwashing behavior, as well as for obtaining data of how to best motivate toilet or urinal users to wash their hands more frequently. By for example comparing various kinds of first and/or second signals, and/or the accumulated number of first signals to the number of second signals, it may be possible to conclude on human inclination to wash hand in response to using the toilet or urinal.

In an advantageously alternative embodiment the users may however carry tags and/or bar codes and the system may comprise a corresponding reader for keeping records of the users behavior and intervene if the same person deliberately omits hand washing on multiple occasions. Such a person is a potential contact and contributes to the danger of infection. In particular at hospitals or similar places where the number of potentially infectious persons or patients are considerable the embodiment with tags, such as RFID tags and a corresponding RFID reader, is highly preferred.

The system according to the present invention may advantageously comprise an AD converter to convert an analog signal obtained by the sensor means to a digital signal to be analyzed to identify the signature of a specific toilet or urinal, i.e. its respective sound spectrum. Noise can e.g. be more easily detected in a digital signal as compare to an analog signal because signal to noise ratio are improved. By digitizing the first signal obtained by the sensor means the likelihood of true identifications of use of a toilet or a urinal is highly increased and the risk of false identifications substantially eliminated. By digitizing the first signal more complex sound spectra can also be identified.

Thus digitizing the first signal constitutes an improved means to identify use of a toilet or a urinal in a simple manner as well as to uniquely link use of various toilets and urinals to the system.

The invention also relates to a method for motivating and/or prompting persons to wash hands after having used the toilet.

The method comprises the steps of providing a cleansing agent dispenser, providing sensor means for detecting use of the toilet or urinal, creating by the sensor means a first signal indicative of detection of the use of the toilet or urinal, associating signaling means with the cleansing agent dispenser, and issuing by the signaling means in response to the first signal and actuation of the cleansing agent dispenser a second signal for reminding or prompting persons to use the cleansing, agent dispenser.

In a preferred embodiment of the method according to the present invention the sensor means may be a sound sensor means adapted for recognizing at least a part of a sound spectrum associated with a use of a toilet or a urinal. Preferably such a sound sensor means can be selected to have auditory discrimination ability and determines sound spectra relating to a flushing water in the toilet bowl being hit by either a liquid or solid. Preferably the detected first signal is digitized to be easy to identify among a selection of other signals.

In a particular effective and reliable method according to the present invention the method may comprise the steps of
  in response to positively having detected that a toilet or urinal has been used, emitting an auditory and/or visual reminder signal, and
  deactivating the second signal by actuation of the cleansing agent dispenser.

Deactivation of the second signal is intended to be an action made by the user of the toilet or the urinal, but in case of a false second signal or the second signal has been ignored the second signal can be switched off remotely or just time out after a predetermined period.

To encourage, in particular children, to wash hand effectively actuation of the cleansing agent dispenser may trigger emitting an auditory and/or visual hand wash period signal, such as e.g. for a duration of 1-2 minutes or even longer. If the wash time period signal includes a feature that motivates the child to stay next to the cleansing agent dispenser for a longer time to experience the wash time signal, the child may be motivated to wash hands for the duration of the wash time period signal.

The method may also comprise that the users are equipped with tags and/or bar codes in which case the system may comprise a corresponding reader for keeping records of behavior.

By using the detection of the event that the toilet or urinal having been used, e.g. the flushing of the toilet, to trigger the second signal that is a reminder signal to wash hands, the person that has used the toilet will make efforts to stop the reminder signal before leaving the washroom. The way to do so is simply to actuate the cleansing agent dispenser. In order to prevent cheating and avoidance of hand wash the person needs to move hers/his hands very close to the cleansing agent dispenser, e.g very close to the cleansing agent discharging nozzle, in order to prevent that the person can move hers/his hands away rapidly enough to avoid being hit by the dropping dose of cleansing agent, such as soap. Because the cleansing agent inevitably soils the person in this way she/he will proceed to wash hers/his hands. In a system and method including wash time period signal hand washing is in most cases continued, until the hand wash period signal terminates because she/he will be reluctant and embarrassed to leave the washroom while the hand wash period signal still is going on.

Thus, the system and method according to the present invention is highly motivating and prompts persons to wash hand subsequent to having used the toilet or urinal.

BRIEF DESCRIPTION OF THE DRAWINGS

The invention will be described below by way of an exemplary embodiment with reference to the accompanying drawing, in which FIGS. 3a-3f illustrate six sound spectra of different origin and related to use of various objects and event that might be related to use of a washroom.

DETAILED DESCRIPTION OF THE INVENTION

Below the system and the method according to the present invention is described in relation to a cleansing agent dispenser being a soap dispenser and a toilet facility in the washroom being a toilet. It is to understood that the below detailed description is only exemplary and that the system and method can be modified in any of the ways described above.

Figure 1:
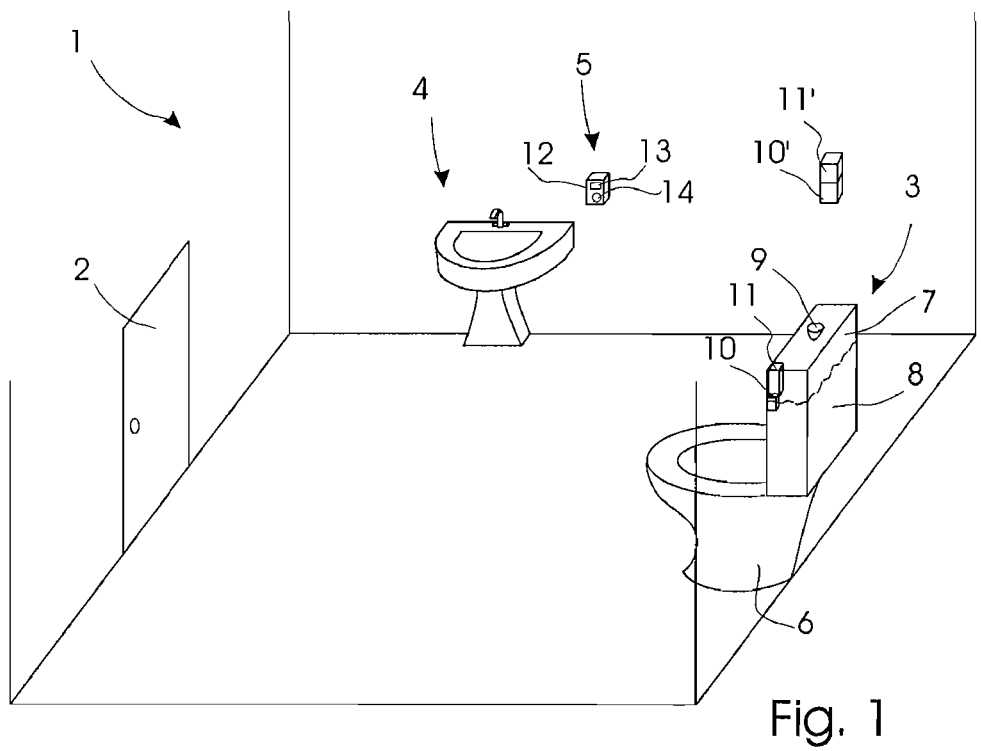
FIG. 1 is a principle sketch of the system according to the present invention.

FIG. 1 shows a washroom 1 with a door 2, a toilet 3, a washbasin 4 and a soap dispenser 5. The toilet 3 has a toilet basin or bowl 6, a cistern 7 with water 8, and an actuator 9 for initiating flushing of the toilet basin or bowl 6. Although the actuator 9 is shown to be a knob, optical flush actuators and other kinds of mechanical actuators can also be used. A sensor means serves for detecting flushing of the toilet 3 and the actuator 9 may in some embodiments form part of the sensor means.

In the embodiment shown in FIG. 1 the sensor means includes a water level sensor 10, which is arranged inside the cistern 7 for detecting a change in the water level in the cistern 7. The detection of the change in the water level activates a first transmitter means 11 to transmit a first signal, which is linked to the operation of the soap dispenser 5.

In an alternative embodiment a sensor means 10' able to detect use of the toilet, e.g. by recognizing the sound of the flushing of the toilet, is situated outside the cistern 7, e.g. in the vicinity of the toilet 3, or is integrated in the soap dispenser 5.

Irrespective of where the sensor means 10;10' is placed, the transmitter means 11 may also be incorporated in the soap dispenser 5 but can also be placed remote from the soap dispenser 5, as indicated in FIG. 1 with the sound sensor 10' and the first transmitter 11' on the wash room wall. The sound sensor 10' and the first transmitter 11' can be in wired or wireless communication with the soap dispenser 5 via a receiver means (not shown) for receiving the transmitted first signal. A remote individual or central control unit (not shown) may control signal capture and transmission. The first transmitter means 11,11' transmits the first signal to second transmission 12 means that actuates a signaling means 13,14 which in a first mode sends out a reminder signal, for example a sound, a movie or another kind of advice of how to wash hands correctly. The second transmission means 12 and the signaling means in form of a display 13 and a loud speaker 14 is incorporated in the soap dispenser 5 and in mutual electronic communication, as indicated with the dotted arrows in the enlarged scale schematic front view of a soap dispenser 5 seen in FIG. 2, as well as the second transmitter means 12 is in electronic communication with the first transmitter means 11, which together with the sensor means also can be integrated in the soap dispenser (not shown). The sensor means may include one or more microphones for receiving and/or detecting the first signal (not shown) originating from use of the toilet. Preferably said detected analog audio signal is digitized and compared to known digital signature, e.g. in a signature database of various relevant sound spectra, to confirm that the first signal originates from use of the toilet, prior to emitting the second signal.

Figure 2:
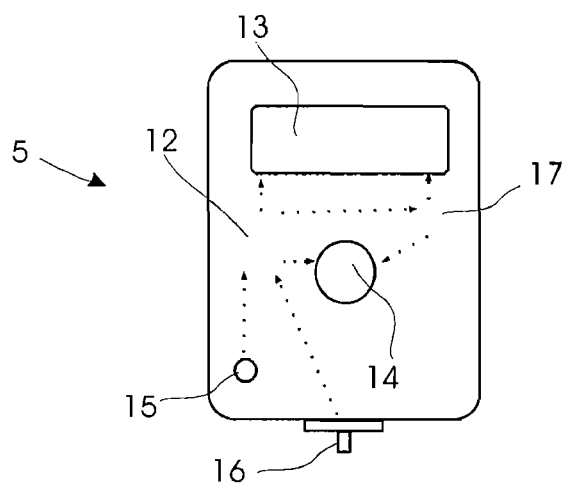
FIG. 2 illustrates an embodiment of a cleansing agent dispenser with sensor means.

The soap dispenser 5 shown in FIG. 2 also has an indicator 15 for indicating low level of soap and power level and a discharge nozzle 16, which can be actuated by application of manual force or be a photoelectric detector coupled to the signaling means and/or to the second transmitter means 12. The second transmitter means 12 can thus just be a switch that switches on the signaling means 13,14 or be part of the signaling means. One or more extra transmitter means, receiver means and/or amplifiers may be provided anywhere in the system to facilitate capturing and transmission of signals and information between the components of the system and the system and the user of the toilet or urinal.

In a preferred embodiment as mentioned above, the sound sensor 10' and the first transmitter means 11' are integrated in the soap dispenser too.

The system may further include a timer 17 for deactivating the reminder signal in case the soap dispenser is never activated. A transmission means included in the soap dispenser may also be adapted to automatically activate the water tap immediately or with a predetermined delay in response to dispensing the dose of soap.

The system may comprise suitable software to control transmission of signals, sensor means, signaling means and activation of mechanical components in the system, as well as an AD converter to promptly and with minimum error convert analog first signal to a digitized signal recognizable as representing the detected relevant use when compared with other digitized signal representing other sound spectra or just compare to a selected one.

FIGS. 3a-f illustrates the difference between six sound spectra of various origins. The sound spectra of FIGS. 3a-c are not directly linked to the use of the toilet or a urinal, contrary to FIGS. 3d-f in which the sound spectra originates from flushing of a urinal and two different kinds of toilets.

FIGS. 3a-f shows the nominal amplitudes of sampled sound signals as a function of time measured in seconds. The sound signals are detected with a microphone at a distance of approximately 1 meter from the objects that constitute the sound sources. The y-axis of the figures shows the nominal amplitude (1 is the saturation level of the AD converter used to convert the analog signal obtained by the microphone to a digital signal). The x-axis shows the time in seconds over which the oscillation of the sound signal is recorded.

As can be seen from FIGS. 3d-3f the sound spectra or sound signals obtained from flushing the toilets and using the urinal all have in common that the amplitudes of the oscillating propagating sound waves, that represents the complex sound spectra, are high or highest at the beginning of the action, which action is triggered by the urination or by the flushing, respectively. Then the amplitude gradually fades away over a period. Just before the oscillation completely fades away a final peak oscillation can be identified, which makes the sound spectrum of flushing the toilets, and thus the toilets audio signature, unique for some toilets in common group, for each toilet and/or for toilets of different origin and operation and function principle. The overall shape of the oscillation is the same and recognizable by the sensor means when comparing to the sound spectrum represented by the noises indicated in FIGS. 3a-3c, from which the signature of the toilets are easy distinguished and discriminated.

A correspondingly composed sound signature can be recognized for the urinal in the period between the 4. second and until about the 10. second of detecting time.

Modifications and combinations of the above principles and designs are foreseen within the scope of the present invention. The various means may be combined in one unit, e.g. if the sensor means is a sound sensor having sound discriminating ability the sound sensor can be included in the cleansing agent dispenser together with all or most other component. The system may be powered entirely or completely by a battery or the power supply network, or combination of these. The battery may be of the chargeable kind and the potential energy stored in the soap in the dispenser and the kinetic energy derivable by the water flow in the toilet used to charge the battery.

By means of the system and the method according to the present invention it is possible in a simple manner to determine the motivating and/or prompting effect of various kinds of second signals and technical means or combinations of these to obtain data for targeting the system and the method to specific needs and/or user group. One kind of second signal may e.g. prove to have a higher level of motivating and/or prompting effect than other kinds of signals for a group of users than for another group of user. For example the system can demonstrate if men are much more susceptible to ignore low sound signals than women, in which case e.g. a urinal implementing the system according to the present invention can be designed and targeted in view of this knowledge and experience to emit a very high and noisy second signal.

Test implementations or other kinds of studies may reveal that a certain user group are prompted best by a visual signal from a light-emitting diode, or that combinations of visual and audible second signals are the only kind of second signals that have reasonable effect. It can for example be verified if simple messages applied to the cleansing agent dispenser have a motivation and/or prompting effect at all, instantaneously or over time. Messages can be simple, such as "Germs kills!" or "Does the person standing next to you wash hands?".

The inventive system and method thus allows to test if a simple visual series of instruction pictures or short messages can stand alone as the sole means for motivation and/or prompting persons to wash hands. Thus use of the system and method according to the present invention provides the unique opportunity to make systems that are tailored, designed and adapted in response to knowledge of one or more main user groups of a toilet or urinal. For example men need other kind of second signals than women, old people other kinds of second signals than children, and within the scope of the present invention factors such as level, intensity, duration and/or kind of second signals can be targeted to the specific user group in order to increase overall hygienic behavior locally and globally.

Thus, the system and method according to the present invention is able to measure its own efficiency.

What is claimed is:

1. A system for motivating or prompting persons to wash hands after having used a toilet or urinal, comprising:
    sensor means for detecting use of the toilet or urinal, which sensor means is mounted in proximity of the toilet or urinal and creates a first signal indicative of the use that has been detected,
    signaling means for issuing at least one second signal in response to the first signal for reminding or prompting persons to use a cleansing agent dispenser after using the toilet or urinal, and
    first transmitter means for transmitting the first signal obtained by the sensor means to the signaling means;
    wherein the signaling means is provided in or on the cleansing agent dispenser,
    wherein the system comprises a second transmitter means for, in response to actuation of the cleansing agent dispenser, transmitting an additional second signal to the signaling means to indicate that a dose of cleansing agent has been dispensed, thus indicating that the person has washed his or her hands, and
    wherein the sensor means comprises sound sensor means for detecting and recognizing at least a part of a sound spectrum associated with the use of the toilet or urinal, which sound sensor means creates the first signal when the sound spectrum has been detected.

2. The system according to claim 1, further comprising switching means to switch off the second signal upon actuation of the cleansing agent dispenser to dispense the cleansing agent.

3. The system according to claim 1, wherein the sound sensor means is selected to have auditory discrimination ability to determine sound spectra relating to at least flushing water from a toilet bowl or a urinal bowl.

4. The system according to claim 1, wherein the sound sensor means is selected to have auditory discrimination ability to determine sound spectra relating at least to water being hit by either a liquid or a solid, or flushing of the toilet or the urinal.

5. The system according to claim 1, wherein the sensor means is or comprises a water level sensor.

6. The system according to claim 1, further comprising means for emission of a wash time period signal upon actuation of the cleansing agent dispenser to dispense the cleansing agent.

7. The system according to claim 6, wherein either a reminder signal or the wash time period signal are signals detectable by auditory sense, sight or a combination thereof.

8. The system according claim 1, further comprising one of a display for displaying visual information or a loud speaker for providing audible information.

9. The system according to claim 1, wherein the signaling means comprises a timer.

10. The system according to claim 1, further comprising a control unit for controlling or setting parameters of the system.

11. The system according to claim 1, wherein the sensor means is provided in or on the cleansing agent dispenser.

12. The system according to claim 1, wherein either of the first transmitter means or the second transmitter means is provided in or on the cleansing agent dispenser.

13. The system according to claim 1, further comprising a cabinet for the cleansing agent dispenser.

14. The system according to claim 1, wherein the sound sensor means comprises at least one microphone.

15. The system according to claim 1, wherein the sound sensor means comprises at least two microphones arranged to receive sound spectra from different directions.

16. The system according to claim 1, further comprising a database of sound spectra representative of sound spectra associated with the use of the toilet or the urinal.

17. The system according to claim 1, further comprising recording means for recording a sound spectrum associated with one or more specific uses of a specific toilet or a specific urinal.

18. The system according to claim 17, wherein the recording means records the sound spectrum representative for one or more specific uses of the specific toilet or urinal.

19. The system according to claim 17, wherein the sound spectrum is recorded for a period sufficient to provide a sound spectrum indicative of the specific use, which period is one of at least 0.5 second, at least 0.7 second or at least 1.0 second.

20. The system according to claim 1, wherein the sound sensor means or a control unit therefor is configured to compare and differentiate between the sound spectra detected in different directions by the sensor means.

21. The system according to claim 1, wherein the sound sensor means or a control unit therefor is configured to select the one of the two sound spectra coming from different directions that represents the sound spectrum representative of use of the toilet or urinal.

22. The system according to claim 17, further comprising storage means for storage of recorded sound spectra.

23. The system according to claim 1, wherein the cleansing agent is a liquid soap, an alcohol, an alcohol containing gel, or combinations thereof.

24. The system according to claim 1, wherein the toilet or urinal is one that utilizes water flushing.

25. The system according to claim 1, wherein the system does not include motion sensors for detection of motion of a person in the vicinity of the toilet or urinal or in the vicinity of the cleansing agent dispenser.

26. The system according to claim 1, comprising an AD converter.

27. A method for motivating or prompting persons to wash hands after having used a toilet or urinal, which comprises the steps of:
providing a cleansing agent dispenser,
providing sensor means for detecting use of the toilet or urinal,
creating by the sensor means a first signal indicative of detection of the use of the toilet or urinal,
providing signaling means in or on the cleansing agent dispenser, and
issuing by the signaling means in response to receipt of the first signal a second signal for reminding or prompting persons to use the cleansing agent dispenser,
transmitting an additional second signal to the signaling means upon actuation of the cleansing agent dispenser to indicate that a dose of cleansing agent has been dispensed, thus indicating that the person has washed his or her hands,
wherein the sensor means comprises sound sensor means for detecting and recognizing at least a part of a sound spectrum associated with the use of the toilet or urinal, which sound sensor means creates the first signal when the sound spectrum has been detected.

28. The method according to claim 27, which further comprises selecting the sound sensor means to have auditory discrimination ability and determining sound spectra relating to water in the toilet bowl being hit by either a liquid or solid.

29. The method according to claim 27, which further comprises the steps of:
in response to positively having detected that a toilet or urinal has been used, emitting an auditory or visual reminder signal, and
deactivating the second signal for reminding or prompting persons to use the cleansing agent dispenser by actuation of the cleansing agent dispenser.

30. The method according to claim 27, wherein actuation of the cleansing agent dispenser triggers the emitting of an auditory or visual hand wash period signal.

31. The method according to claim 27, which further comprises equipping users of the toilet or urinal with tags or a bar code and providing a corresponding reader for keeping records of behavior.

32. The system of claim 1 wherein actuation of the cleansing agent dispenser deactivates the second signal.

* * * * *

UNITED STATES PATENT AND TRADEMARK OFFICE
CERTIFICATE OF CORRECTION

| | | |
|---|---|---|
| PATENT NO. | : 8,648,724 B2 | Page 1 of 1 |
| APPLICATION NO. | : 13/421763 | |
| DATED | : February 11, 2014 | |
| INVENTOR(S) | : Lars Forsberg et al. | |

It is certified that error appears in the above-identified patent and that said Letters Patent is hereby corrected as shown below:

Title Page:
Before Item (30) Foreign Application Priority Data, insert Item (63):
-- Related U.S. Application Data
  (63) Continuation of application No. PCT/DK 2010/050238 filed Sep. 16, 2010 --.

Signed and Sealed this
Sixth Day of May, 2014

Michelle K. Lee
*Deputy Director of the United States Patent and Trademark Office*